United States Patent
Kocen et al.

(10) Patent No.: US 12,122,758 B2
(45) Date of Patent: *Oct. 22, 2024

(54) CROWN ETHER AMINES AND METHODS OF USE

(71) Applicant: Pall Corporation, Port Washington, NY (US)

(72) Inventors: Andrew Kocen, Port Washington, NY (US); Rehanah Sejoubsari, Port Washington, NY (US); Ahmad Arabi Shams Abadi, Port Washington, NY (US)

(73) Assignee: Pall Corporation, Port Washington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,305

(22) Filed: Sep. 5, 2023

(65) Prior Publication Data

US 2024/0158366 A1    May 16, 2024

Related U.S. Application Data

(63) Continuation of application No. 17/981,162, filed on Nov. 4, 2022, now Pat. No. 11,787,777.

(51) Int. Cl.
| | |
|---|---|
| *C07D 323/00* | (2006.01) |
| *B01D 53/22* | (2006.01) |
| *B01D 71/06* | (2006.01) |

(52) U.S. Cl.
CPC ......... *C07D 323/00* (2013.01); *B01D 53/228* (2013.01); *B01D 71/06* (2013.01)

(58) Field of Classification Search
CPC .................................................. C07D 323/00
See application file for complete search history.

(56) References Cited

U.S. PATENT DOCUMENTS

| | | | |
|---|---|---|---|
| 4,504,368 A | 3/1985 | Delton et al. | |
| 5,425,878 A | 6/1995 | Lurin et al. | |
| 6,468,657 B1 | 10/2002 | Hou et al. | |
| 9,786,941 B2 | 10/2017 | Fuller et al. | |
| 11,020,713 B2 | 6/2021 | Demeter et al. | |
| 11,787,777 B1 * | 10/2023 | Kocen | B01D 71/06 549/352 |

FOREIGN PATENT DOCUMENTS

| | | |
|---|---|---|
| KR | 2019-0010382 A | 1/2019 |
| KR | 10-1987667 B1 | 6/2019 |

OTHER PUBLICATIONS

Registry No. 300590-59-4, which entered STN on Oct. 31, 2000 (Year: 2000).

* cited by examiner

*Primary Examiner* — Matthew P Coughlin
(74) *Attorney, Agent, or Firm* — Leydig, Voit & Mayer, Ltd.

(57) ABSTRACT

The invention provides a material comprising (i) a crown ether of formula (I) and/or (ii) a crown ether of formula (II), or a salt thereof, wherein each m independently is an integer from 1 to 8, each " ⁀ " designates an optionally present bond and/or structure, each X independently is —$N(R_1)_2$, —$N^*(R_1)$, —$N^{**}$, —$N^*(R_1)_2{}^+Z^-$, or —$N^{**}(R_1)^+Z^-$, provided at least one X is —$N^*(R_1)$, —$N^{**}$, —$N^*(R_1)_2{}^+Z^-$, or —$N^{**}(R_1)^+Z^-$, wherein each $R_1$ independently is hydrogen or $C_{1-6}$ alkyl, each Z is optionally present and independently is a counterion to balance the charge on nitrogen, and * represents a bond to a remainder of the material, a method of making the material, and a method of using the material.

18 Claims, 1 Drawing Sheet

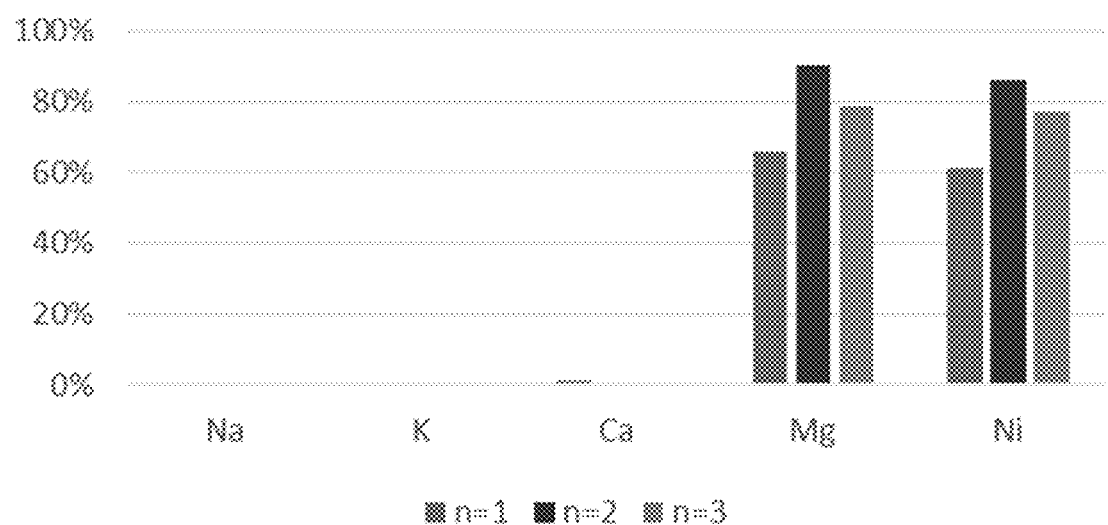

CROWN ETHER AMINES AND METHODS OF USE

CROSS-REFERENCE TO RELATED APPLICATIONS

This patent application is a continuation of copending U.S. patent application Ser. No. 17/981,162, filed Nov. 4, 2022, which is incorporated by reference.

BACKGROUND OF THE INVENTION

Crown ethers are cyclic organic molecules containing oxygen- and carbon-based repeating units. Crown ethers are known to strongly bind certain cations to form a complex. In this regard, the oxygen atoms are oriented in a manner to coordinate with a metal cation located at the interior of the ring, whereas the exterior of the ring remains hydrophobic due to the repeating carbon units. As a result, the complex, including the crown ether and the cation, may be soluble in nonpolar solvents. For this reason crown ethers may be useful in phase transfer catalysis.

Due to the high utility of crown ether-based compounds there remains a need for the development of materials comprising crown ether-based compounds, as well as new and efficient ways to prepare such materials. The invention provides such materials and methods of preparation. Additional benefits and aspects of the invention will be readily apparent from the disclosure provided herein.

BRIEF SUMMARY OF THE INVENTION

The invention provides a material comprising (i) a crown ether of formula (I):

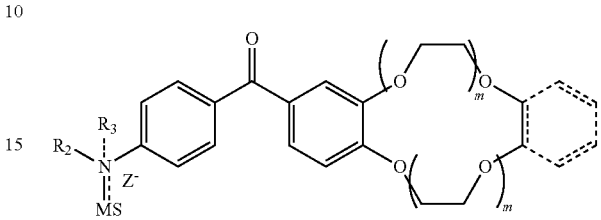

and/or (ii) a crown ether of formula (II):

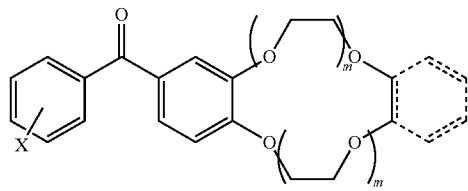

or a salt thereof, wherein each m independently is an integer from 1 to 8, each "⁓" designates an optionally present bond and/or structure, each X independently is —N(R$_1$)$_2$, —N*(R$_1$), —N**, —N*(R$_1$)$_2$$^+$Z$^-$, or —N**(R$_1$)$^+$Z$^-$, provided at least one X is —N*(R$_1$), —N**, —N*(R$_1$)$_2$$^+$Z$^-$, or —N**(R$_1$)$^+$Z$^-$, wherein each R$_1$ independently is hydrogen or C$_{1-6}$ alkyl, each Z is optionally present and independently is a counterion to balance the charge on nitrogen, and * represents a bond to a remainder of the material.

The invention also provides a material of formula (III):

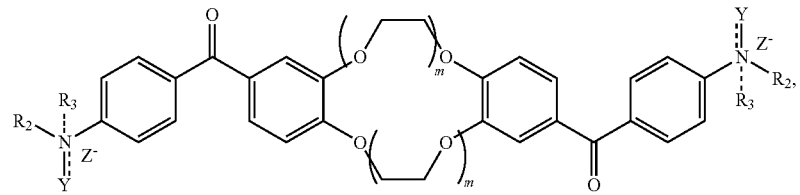

or formula (IV):

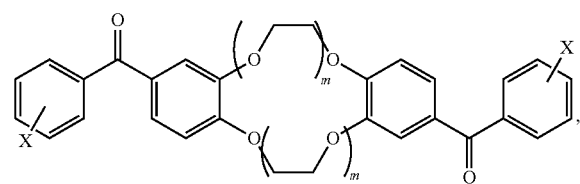

or a salt thereof, wherein each m independently is an integer from 1 to 8, each R$_2$ is optionally present and independently is hydrogen or C$_{1-6}$ alkyl, each "⁓" designates an optionally present bond and/or structure, each R$_3$ is optionally present and independently is hydrogen, C$_{1-6}$ alkyl, or MS, each Z is optionally present and independently is a counterion to balance the charge on nitrogen, each Y is R$_2$ or MS, provided that at least one Y is MS, and each MS independently is a macromolecular support selected from a membrane, a fibrous media, a polymeric coating or material, a metal organic framework, a monolith support, a bead, a filter, or a resin.

The invention further provides a method of making a material described herein, the method comprising: (i) reacting a benzo or dibenzo crown ether with an aminobenzoic acid compound to form (a) a crown ether of formula (V):

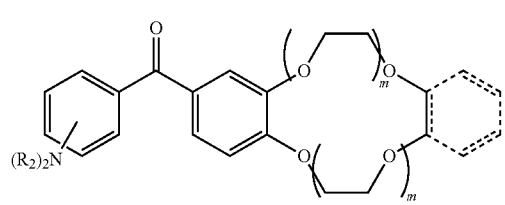

or (b) a crown ether of formula (VI):

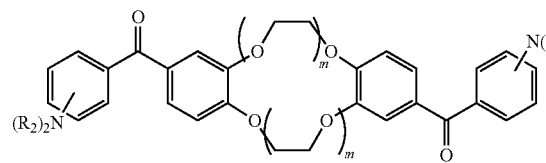

and (ii) reacting the crown ether of formula (V) or the crown ether of formula (VI) with a macromolecular support to form at least one C—N bond or C=N bond.

The invention further provides a method of removing one or more metal ions from a solution comprising passing the solution through a material described herein.

BRIEF DESCRIPTION OF THE DRAWINGS

The FIGURE provides a bar graph showing the metal removal efficiency (MRE) percentage of sodium, potassium, calcium, magnesium, and nickel for three trials (n=1-3) exhibited by a crown ether amine resin, as described in Example 5.

DETAILED DESCRIPTION OF THE INVENTION

The invention provides a material comprising (i) a crown ether of formula (I):

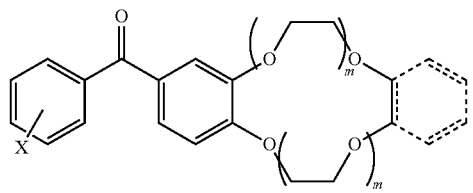

and/or (ii) a crown ether of formula (II):

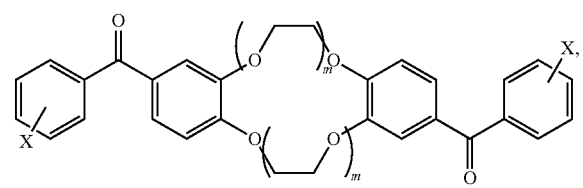

or a salt thereof, wherein each m independently is an integer from 1 to 8, each "⁀" designates an optionally present bond and/or structure, each X independently is —N($R_1$)$_2$, —N*($R_1$), —N**, —N*($R_1$)$_2$$^+$Z$^-$, or —N**($R_1$)$^+$Z$^-$, provided at least one X is —N*($R_1$), —N**, —N*($R_1$)$_2$$^+$Z$^-$, or —N**($R_1$)$^+$Z$^-$, wherein each $R_1$ independently is hydrogen or $C_{1-6}$ alkyl, each Z is optionally present and independently is a counterion to balance the charge on nitrogen, and * represents a bond to a remainder of the material.

In some embodiments, the material comprises a crown ether of formula (I):

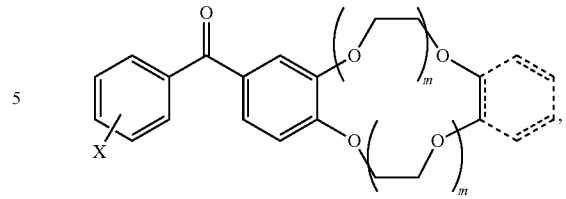

or a salt thereof, wherein each m independently is an integer from 1 to 8 (e.g., 1, 2, 3, 4, 5, 6, 7, or 8), each "⁀" designates an optionally present bond and/or structure, and X is —N*($R_1$), —N**, —N*($R_1$)$_2$$^+$Z$^-$, or —N**($R_1$)$^+$Z$^-$, wherein each $R_1$ independently is hydrogen or $C_{1-6}$ alkyl, Z is an optionally present counterion to balance the charge on nitrogen, and * represents a bond to a remainder of the material.

In some embodiments, the material comprises a crown ether of formula (II):

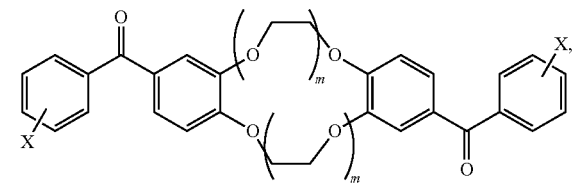

or a salt thereof, wherein each m independently is an integer from 1 to 8 (e.g., 1, 2, 3, 4, 5, 6, 7, or 8), each X independently is —N($R_1$)$_2$, —N*($R_1$), —N**, —N*($R_1$)$_2$$^+$Z$^-$, or —N**($R_1$)$^+$Z$^-$, provided at least one X is —N*($R_1$), —N**, —N*($R_1$)$_2$$^+$Z$^-$, or —N**($R_1$)$^+$Z$^-$, wherein each $R_1$ independently is hydrogen or $C_{1-6}$ alkyl, each Z is optionally present and independently is a counterion to balance the charge on nitrogen, and * represents a bond to a remainder of the material.

In any of the embodiments of the material, described herein, each m independently is an integer from 1 to 8 (e.g., 1, 2, 3, 4, 5, 6, 7, or 8). Generally, each m is selected from an integer from 1 to 8 so as to provide a crown ether selected from 12-crown-4, 15-crown-5, 18-crown-6, 21-crown-7, 24-crown-8, 27-crown-9, or 30-crown-10. For example, each m can be 2 so as to provide 12-crown-4, each m can be 3 so as to provide 18-crown-6, each m can be 4 so as to provide 24-crown-8, or each m can be 5 so as to provide 30-crown-10. Alternatively, or additionally, each m can be different so as to provide 12-crown-4, 15-crown-5, 18-crown-6, 21-crown-7, 24-crown-8, 27-crown-9, or 30-crown-10. In some embodiments, each m independently is an integer from 1 to 4. In certain embodiments, each m independently is an integer selected from 1 or 2. In other embodiments, each m is 2.

In any of the embodiments of the materials, described herein, each X independently is —N($R_1$)$_2$, —N*($R_1$), —N**, —N*($R_1$)$_2$$^+$Z$^-$, or —N**($R_1$)$^+$Z$^-$, provided at least one X is —N*($R_1$), —N**, —N*($R_1$)$_2$$^+$Z$^-$, or —N**($R_1$)$^+$Z$^-$, wherein each $R_1$ independently is hydrogen or $C_{1-6}$ alkyl, Z is an optionally present counterion to balance the charge on nitrogen, and * represents a bond to a remainder of the material. In other words, the crown ether of formula (I) or crown ether of formula (II) can be bound to the remainder for the material via a single bond, multiple single bonds, a double bond, or multiple double bonds, thereby forming structures such as amines, imines, amides, and the like. For example, the crown ether of formula (I) or crown ether of formula (II) can be incorporated into the material at a single location via one or two bonds such that the nitrogen atom has a neutral charge or a cationic charge. Alternatively, or additionally, the crown ether of formula (I) or crown ether of formula (II) can be incorporate into the material at multiple locations via one or two bonds at each location such that the nitrogen atoms have a neutral charge or a cationic charge. It will be readily understood by a person of ordinary skill in the art that multiple crown ethers of formula (I) or crown ethers of formula (II) can be incorporated into the material.

In some embodiments, each X independently is —N(R$_1$)$_2$, —N*(R$_1$), or —N** provided at least one X is —N*(R$_1$) or —N**, wherein each R$_1$ independently is hydrogen or C$_{1-6}$ alkyl, and * represents a bond to a remainder of the material. For example, each X can be —N(R$_1$)$_2$ or —N*(R$_1$) provided at least one X is —N*(R$_1$), wherein each R$_1$ independently is hydrogen or C$_{1-6}$ alkyl, and * represents a bond to a remainder of the material. In other embodiments, each X independently is —N(R$_1$)$_2$ or —N provided at least one X is —N, wherein each R$_1$ independently is hydrogen or C$_{1-6}$ alkyl, and * represents a bond to a remainder of the material. In certain embodiments, each X independently is —N(R$_1$)$_2$ or —N*(R$_1$), provided at least one X is —N*(R$_1$), such that the crown ether of formula (I) or crown ether of formula (II) can be bound to the remainder for the material via a single bond (e.g., to form an amine or amide).

In other embodiments, each X independently is —N(R$_1$)$_2$, —N*(R$_1$), or —N**(R$_1$)$^+$Z$^-$, provided at least one X is —N*(R$_1$)$_2$$^+$Z$^-$ or N**(R$_1$)$^+$Z$^-$, wherein each R$_1$ independently is hydrogen or C$_{1-6}$ alkyl, Z is an optionally present counterion to balance the charge on nitrogen, and * represents a bond to a remainder of the material.

In any of the embodiments of the materials, described herein, each R$_1$ independently is hydrogen or C$_{1-6}$ alkyl (e.g., methyl, ethyl, propyl, butyl, pentyl, or hexyl). In some embodiments, each R$_1$ is hydrogen. In other embodiments, each R$_1$ is C$_{1-6}$ alkyl.

In any of the embodiments of the material, described herein, each " " designates an optionally present bond and/or structure. In other words, the bond to variable Y can be a single bond or a double bond depending on whether Y is R$_2$ or MS and the bond to MS can be a single bond or a double bond such that one of the bonds is optionally present, and the phenyl ring designated by the dashed lines is optionally present.

In any of the embodiments of the material described herein, each * independently a bond to a remainder of the material, provided that at least one * is present. The bond to the remainder of the material can be any suitable bond so long as at least one bond is a C—N bond or C═N bond. In some embodiments, the material comprising a crown ether of formula (I) or a crown ether of formula (II) has more than one C—N bond or C═N bond with the remainder of the material. For example, the crown ether can (i) be bound to the remainder of the material via two separate nitrogen atoms as (a) two separate *s or (b) two separate **s and/or (ii) be bound to the remainder of the material via a single nitrogen as (a) one single *, (b) two separate *s, or (c) a single . Thus,  as used herein refers to two separate single bonds or one single double bond.

In any of the embodiments of the material, described herein, each Z is optionally present and independently is a counterion to balance the charge on nitrogen. Z can be any suitable counterion to balance the cationic charge on the nitrogen atom. For example, Z can be a halogen (e.g., chlorine, bromine, or iodine), NO$_3$$^-$, OH$^-$, or the like. In some embodiments, Z is a halogen (e.g., chlorine or bromine).

The crown ether of formula (I) or crown ether of formula (II) can be incorporated into any suitable material (e.g., chemical compound or media) so long as the crown ether of formula (I) or crown ether of formula (II) is bound to the remainder of the material via at least one bond is a C—N bond or C═N bond designated with an * in formulae (I) and (II). It will be readily understood to a person of ordinary skill in the art that the crown ether of formula (I) or crown ether of formula (II) can be incorporated into the material any number of times at any number of locations. Thus, the material can be any suitable material (e.g., chemical compound or media) capable of forming at least one C—N bond or C═N bond with the crown ether of formula (I) or crown ether of formula (II). In some embodiments, the material is porous such that a liquid or fluid can be passed through the material.

In some embodiments, the remainder of the material to which the crown ether of formula (I) or crown ether of formula (II) is bound to a macromolecular support selected from a membrane (e.g., a porous membrane or a permeable membrane), a fibrous media, a polymeric coating (e.g., a laminate or sealant such as a polyurethane coating, an epoxy coating, an acrylic coating, etc.) or material (e.g., gelatin, alginate, starch, polyethylene, polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide, polyimide, polyester, cellulose, polystyrene, etc.), a metal organic framework, a monolith support (e.g., a catalyst support), a bead (e.g., a polymeric bead), a filter, or a resin (e.g., a chromatographic resin). In some embodiments, the macromolecular support comprises gelatin, alginate, starch, polyethylene (e.g., high density polyethylene), polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide (e.g., nylon), polyimide, polyester, cellulose, polystyrene, or a combination thereof. In certain embodiments, the macromolecular support comprises polyacrylonitrile, poly(meth)acrylate, poly(meth)acrylamide, polyimide, polyester, polystyrene, or a combination thereof.

In certain embodiments, the crown ether compounds described herein are used to functionalize coatings such as those containing benzyl chloride groups. Alternatively, or additionally, the crown ether compounds described herein can be converted directly into polyamides or polyimides through a polymerization reaction.

Thus, in some embodiments, the material is of formula (III):

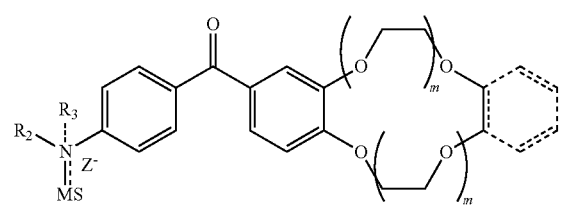

or formula (IV):

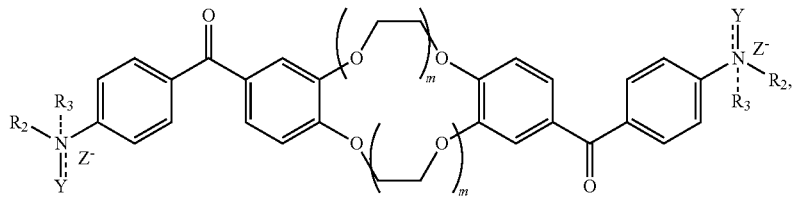

or a salt thereof, wherein each m independently is an integer from 1 to 8, each $R_2$ is optionally present and independently is hydrogen or $C_{1-6}$ alkyl, each "⌇" designates an optionally present bond and/or structure, each $R_3$ is optionally present and independently is hydrogen, $C_{1-6}$ alkyl, or MS, each Z is optionally present and independently is a counterion to balance the charge on nitrogen, each Y is $R_2$ or MS, provided that at least one Y is MS, and each MS independently is a macromolecular support selected from a membrane, a fibrous media, a polymeric coating or material, a metal organic framework, a monolith support, a bead, a filter, or a resin. All other definitions and embodiments, with respect to variables m, $R_2$, $R_3$, Y, and Z and the macromolecular support are as described herein with respect to the inventive material.

In any of the embodiments of the material described herein, each Y is $R_2$ or MS, provided that at least one Y is MS. In other words, the materials described herein have a least one C—N bond or C=N bond formed with the crown ether of formula (I) or crown ether of formula (II).

In any of the embodiments of the materials, described herein, each $R_2$ is optionally present and independently is hydrogen or $C_{1-6}$ alkyl (e.g., methyl, ethyl, propyl, butyl, pentyl, or hexyl). In some embodiments, each $R_2$ is hydrogen. In other embodiments, each $R_2$ is $C_{1-6}$ alkyl. In certain embodiments, $R_2$ is not present.

In any of the embodiments of the materials, described herein, each $R_3$ is optionally present and independently is hydrogen, $C_{1-6}$ alkyl (e.g., methyl, ethyl, propyl, butyl, pentyl, or hexyl), or MS. In some embodiments, each $R_3$ is not present. In other embodiments, each $R_3$ is $C_{1-6}$ alkyl. When $R_3$ is present, the nitrogen atom of the crown ether may have a positive charge. The positive charge may or may not be balanced with an anionic charge provided by counterion Z, described herein. Without wishing to be bound by any particular theory, it is believed that the charged variant of the crown ether modifies the material to behave like an exchange resin, which may be desirable for certain applications.

In some embodiments, the material is of formula (III):

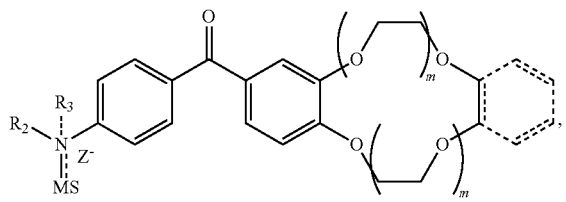

or a salt thereof, wherein each m independently is an integer from 1 to 8, $R_2$ is optionally present and is hydrogen or $C_{1-6}$ alkyl, each "⌇" designates an optionally present bond and/or structure, $R_3$ is optionally present and is hydrogen, $C_{1-6}$ alkyl, or MS, Z is optionally present and is a counterion to balance the charge on nitrogen, and each MS independently is a macromolecular support selected from a membrane, a fibrous media, a polymeric coating or material, a metal organic framework, a monolith support, a bead, a filter, or a resin. All other definitions and embodiments, with respect to variables m, $R_2$, $R_3$, and Z and the macromolecular support are as described herein with respect to the inventive material.

In other embodiments, the material is of formula (IV):

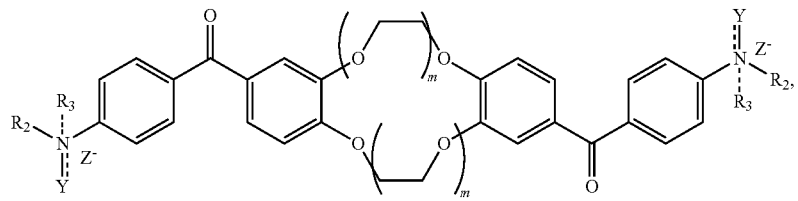

or a salt thereof, wherein each m independently is an integer from 1 to 8, each $R_2$ is optionally present and independently is hydrogen or $C_{1-6}$ alkyl, each "⌇" designates an optionally present bond and/or structure, each $R_3$ is optionally present and independently is hydrogen, $C_{1-6}$ alkyl, or MS, each Z is optionally present and independently is a counterion to balance the charge on nitrogen, each Y is $R_2$ or MS, provided that at least one Y is MS, and each MS independently is a macromolecular support selected from a membrane, a fibrous media, a polymeric coating or material, a metal organic framework, a monolith support, a bead, a filter, or a resin. All other definitions and embodiments, with respect to variables m, $R_2$, $R_3$, Y, and Z and the macromolecular support are as described herein with respect to the inventive material.

It is an objective of the present application that the crown ether of formula (I) or crown ether of formula (II) is incorporated into the material via a C—N bond or C═N bond. Thus, the invention also provides a method of making a material described, the method comprising:

(i) reacting a benzo or dibenzo crown ether with an aminobenzoic acid compound to form (a) a crown ether of formula (V):

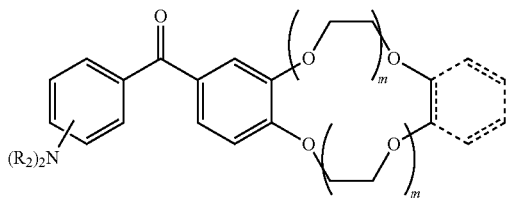

or (b) a crown ether of formula (VI):

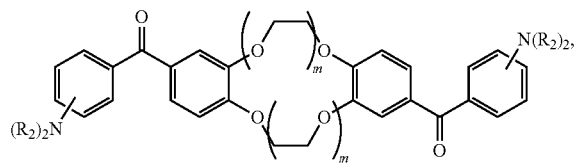

and (ii) reacting the crown ether of formula (V) or the crown ether of formula (VI) with a macromolecular support selected from a membrane, a fibrous media, a polymeric coating or material, a metal organic framework, a monolith support, a bead, a filter, or a resin to form at least one C—N bond or C═N bond. All other definitions and embodiments, with respect to variables m and $R_2$ and the macromolecular support are as described herein with respect to the inventive material.

The method reacting a benzo or dibenzo crown ether with an aminobenzoic acid compound to form a crown ether of formula (V) or a crown ether of formula (VI). For example, the amino benzoic acid compound can be combined (e.g., contacted), mixed (e.g., shaken, stirred, etc.) heated, refluxed, or a combination thereof with a benzo or dibenzo crown ether for any duration of time so long as the desired crown ether of formula (V) or a crown ether of formula (VI) is formed.

The aminobenzoic acid compound can be any suitable benzoic acid so long as the aryl ring has an amine-based substituent. For example, the aminobenzoic acid compound can be 2-aminobenzoic acid, 2-(methylamino)benzoic acid, 2-(dimethylamino)benzoic acid, 3-aminobenzoic acid, 3-(methylamino)benzoic acid, 3-(dimethylamino)benzoic acid, 4-aminobenzoic acid, 4-(methylamino)benzoic acid, 4-(dimethylamino)benzoic acid, or a combination thereof. In some embodiments, the aminobenzoic acid compound is 4-aminobenzoic acid, 4-(methylamino)benzoic acid, 4-(dimethylamino)benzoic acid, or a combination thereof. In certain embodiments, the aminobenzoic acid compound is 4-aminobenzoic acid. In other embodiments, the aminobenzoic acid compound is 4-(methylamino)benzoic acid.

The aminobenzoic acid compound can be used in any suitable amount. Generally, the aminobenzoic acid compound is added in slight excess (e.g., about 1 molar equivalent, about 1.05 molar equivalents, about 1.1 molar equivalent, about 1.15 molar equivalents, or about 1.2 molar equivalents) to the number of ketone moieties desired. Thus, in some embodiments, the aminobenzoic acid compound is added in an amount of at least 1×, at least 1.05×, at least 1.1×, at least 1.15×, or at least 1.2×molar equivalents relative to the number of ketone moieties desired.

In some embodiments, the crown ether of formula (V) or the crown ether of formula (VI) is formed in a solvent. Thus, the reaction between the benzo or dibenzo crown ether and the aminobenzoic acid compound can be performed in any suitable solvent. In some embodiments, the solvent is a high boiling solvent (i.e., greater than 100° C.) such as toluene or the like. In other embodiments, the formation of the crown ether of formula (V) or the crown ether of formula (VI) is carried out in a low boiling solvent (i.e., less than 100° C.) such as diethyl ether, tetrahydrofuran, ethanol, methanol, acetonitrile, dichloromethane, or the like.

In some embodiments, the formation of the crown ether of formula (V) or the crown ether of formula (VI) is facilitated by an acid promoter and/or heat. The acid promoter can be any suitable BrØnsted acid or Lewis acid. For example, the formation of the crown ether of formula (V) or the crown ether of formula (VI) can be facilitated by polyphosphoric acid, phosphorus pentoxide, boron trifluoride, sulfuric acid, aluminum chloride, Eaton's reagent, or the like. In certain embodiments, the formation of the crown ether of formula (V) or the crown ether of formula (VI) is facilitated Eaton's reagent. The reaction can be heated to any suitable temperature. For example, the reaction between the benzo or dibenzo crown ether and the aminobenzoic acid compound can be heated to about 25° C. or higher, about 50° C. or higher, about 75° C. or higher. In certain embodiments, the reaction between the benzo or dibenzo crown ether and the aminobenzoic acid compound is heated to a temperature of about 25° C. to about 100° C.

The method further comprises reacting the crown ether of formula (V) or the crown ether of formula (VI) with a macromolecular support selected from a membrane, a fibrous media, a polymeric coating or material, a metal organic framework, a monolith support, a bead, a filter, or a resin to form at least one C—N bond or C═N bond. For example, the crown ether of formula (V) or the crown ether of formula (VI) can be combined (e.g., contacted), mixed (e.g., shaken, stirred, etc.) heated, refluxed, or a combination thereof with the macromolecular support for any duration of time so long as the desired C—N bond or C═N bond is formed. The desired C—N bond or C═N bond can be formed by any suitable means, many of which are known in the art. For example, the C—N bond or C═N bond can be formed by a displacement reaction, condensation reaction, or reductive amination reaction.

The materials described herein can be used in any suitable industrial application for any suitable purpose. For example, the materials described herein can be used in water purification applications, wastewater treatment applications, mining applications, electronic (e.g., microelectronic) applications, papermaking applications, pharmaceutical applications, biomedical applications, energy applications (e.g., as separators in fuel cells or batteries), or metallurgy applications. Generally, the materials described herein are used to selectively remove one or more metal ions from a fluid (i.e., solution). The fluid can be any suitable liquid containing a solvent (e.g., water, alcohols, sulfoxides, sulfides, acetates, ethers, amides, nitriles, or a combination thereof) and one or more metal ions. In certain embodiments, the fluid (i.e., solution) is an aqueous solution.

In some embodiments, the materials described herein can be used in a method of removing one or more metal ions from a solution comprising passing the solution through the material. For example, the material can be used as a filter, porous media, chromatographic resin, membrane, or the like through which the solution passes to remove one or more metal ions. Thus, the invention further provides a method of removing one or more metal ions from a solution comprising passing the solution through a material comprising (i) a crown ether of formula (I):

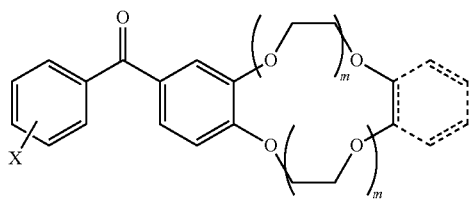

and/or (ii) a crown ether of formula (II):

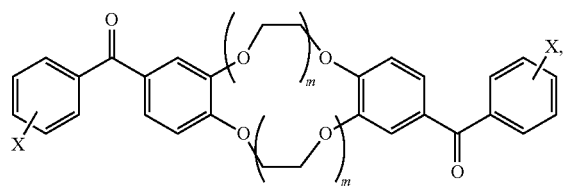

or a salt thereof, wherein each m independently is an integer from 1 to 8, each "⌇" designates an optionally present bond and/or structure, each X independently is —$N(R_1)_2$, —$N*(R_1)$, —$N**$, —$N*(R_1)_2{}^+Z^-$, or —$N**(R_1)^+Z^-$, provided at least one X is —$N*(R_1)$, —$N**$, —$N*(R_1)_2{}^+Z^-$, or —$N**(R_1)^+Z^-$, wherein each $R_1$ independently is hydrogen or $C_{1-6}$ alkyl, Z is an optionally present counterion to balance the charge on nitrogen, and * represents a bond to a remainder of the material. All other definitions and embodiments, with respect to variables m and X are as described herein with respect to the inventive material.

The method can be used to remove any suitable ion. Alternatively, or additionally, the method can be used to allow any suitable ion to pass through the material. For example, the method can used to selectively remove one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof. Alternatively, or additionally, the method can be used to selectively allow one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof through the material. In certain embodiments, the method selectively allows for lithium to pass through the material and removes one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

The method can remove any suitable amount of the one or more metal ions from the solution. For example, the method can remove at least 40% of the one or more metal ions from the solution, at least 50% of the one or more metal ions from the solution, at least 60% of the one or more metal ions from the solution, at least 70% of the one or more metal ions from the solution, at least 80% of the one or more metal ions from the solution, or at least 90% of the one or more metal ions from the solution. In some embodiments, the method removes at least 50% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof. In certain embodiments, the method removes at least 60% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof. In preferred embodiments, the method removes at least 70% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

In some embodiments, the solution that passes through the material is the desirable product of the methods described herein. Thus, in such embodiments, the method can further comprise recovering the solution (e.g., aqueous solution) that has been passed through the material. Without wishing to be bound by any particular theory, it is believed that when smaller metal ions such as lithium and/or sodium are desired, the recovered solution will be the desired product since smaller metal ions such as lithium and/or sodium are more likely to pass through the materials described herein.

In other embodiments, the one or more metal ions removed from the solution are the desirable product of the method described herein. Thus, in these embodiments, the method can further comprise recovering the one or more metal ions removed from the solution. The one or more metal ions can be recovered by any suitable means. For example the material containing the one or more metal ions can be washed with a recovery solution. Without wishing to be bound by any particular theory, it is believed that when larger metal ions such as magnesium, aluminum, potassium, calcium, manganese, iron, barium, etc. are desired, these desired metal ions will remain in the material because larger metal ions are less likely to pass through the materials described herein.

Aspects, including embodiments, of the invention described herein may be beneficial alone or in combination, with one or more other aspects or embodiments. Without limiting the foregoing description, certain non-limiting embodiments of the disclosure numbered 1-26 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below:

EMBODIMENTS (1) In embodiment (1) is presented material comprising (i) a crown ether of formula (I):

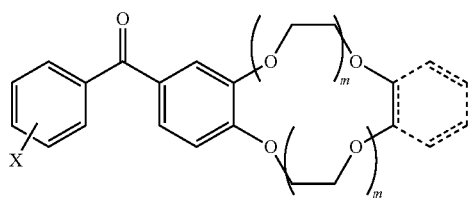

and/or (ii) a crown ether of formula (II):

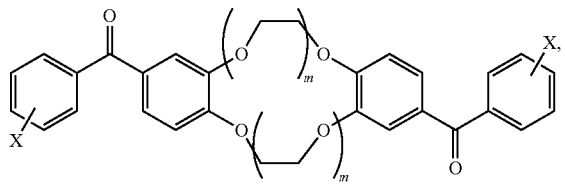

or a salt thereof, herein each m independently is an integer from 1 to 8, each "⌇" designates n optionally present bond and/or structure, each X independently is —N(R$_1$)$_2$, —N*(R$_1$), —N**, —N*(R$_1$)$_2$$^+$Z$^-$, or —N**(R$_1$)$^+$Z$^-$, provided at least one X is —N*(R$_1$), —N**, —N*(R$_1$)$_2$$^+$Z$^-$, or —N**(R$_1$)$^+$Z$^-$, wherein each R$_1$ independently is hydrogen or C$_{1-6}$ alkyl, each Z is optionally present and independently is a counterion to balance the charge on nitrogen, and * represents a bond to a remainder of the material.

(2) In embodiment (2) is presented the material of embodiment (1), wherein the material comprises a crown ether of formula (I):

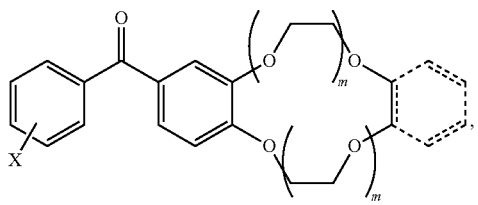

or a salt thereof, wherein each m independently is an integer from 1 to 8, each "⌇" designates an optionally present bond and/or structure, and X is —N*(R$_1$), —N**, —N*(R$_1$)$_2$$^+$Z$^-$, or —N**(R$_1$)$^+$Z$^-$, wherein each R$_1$ independently is hydrogen or C$_{1-6}$ alkyl, Z is an optionally present counterion to balance the charge on nitrogen, and * represents a bond to a remainder of the material.

(3) In embodiment (3) is presented the material of embodiment (1), wherein the material comprises a crown ether of formula (II):

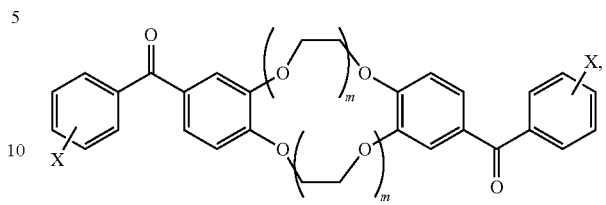

or a salt thereof, wherein each m independently is an integer from 1 to 8, each X independently is —N(R$_1$)$_2$, —N*(R$_1$), —N**, —N*(R$_1$)$_2$$^+$Z$^-$, or —N**(R$_1$)$^+$Z$^-$, provided at least one X is —N*(R$_1$), —N**, —N*(R$_1$)$_2$$^+$Z$^-$, or —N**(R$_1$)$^+$Z$^-$, wherein each R$_1$ independently is hydrogen or C$_{1-6}$ alkyl, each Z is optionally present and independently is a counterion to balance the charge on nitrogen, and * represents a bond to a remainder of the material.

(4) In embodiment (4) is presented the material of any one of embodiments (1)-(3), wherein each m independently is an integer from 1 to 4.

(5) In embodiment (5) is presented the material of embodiments (1)-(4), wherein each m independently is an integer selected from 1 or 2.

(6) In embodiment (6) is presented the material of any one of embodiments (1)-(5), wherein each m is 2.

(7) In embodiment (7) is presented the material of any one of embodiments (1)-(6), wherein each X independently is —N(R$_1$)$_2$, —N*(R$_1$), or —N** provided at least one X is —N*(R$_1$) or —N**, wherein each R$_1$ independently is hydrogen or C$_{1-6}$ alkyl, and * represents a bond to a remainder of the material.

(8) In embodiment (8) is presented the material of embodiment (7), wherein each R$_1$ is hydrogen.

(9) In embodiment (9) is presented the material of embodiment (7), wherein each R$_1$ is C$_{1-6}$ alkyl.

(10) In embodiment (10) is presented the material of embodiment (1), wherein the material is of formula (III):

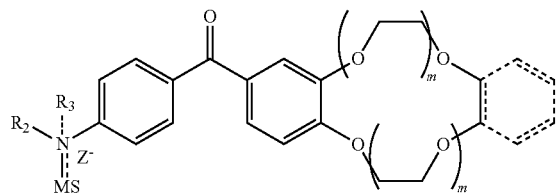

or formula (IV):

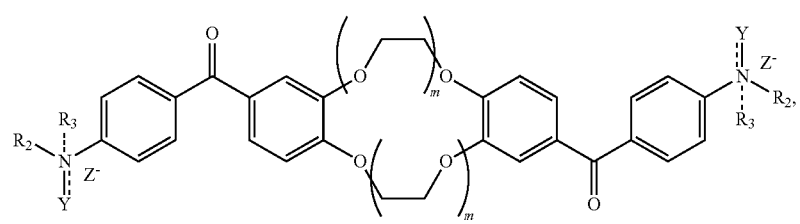

or a salt thereof, wherein each m independently is an integer from 1 to 8, each $R_2$ is optionally present and independently is hydrogen or $C_{1-6}$ alkyl, each "⁓" designates an optionally present bond and/or structure, each $R_3$ is optionally present and independently is hydrogen, $C_{1-6}$ alkyl, or MS, each Z is optionally present and independently is a counterion to balance the charge on nitrogen, each Y is $R_2$ or MS, provided that at least one Y is MS, and each MS independently is a macromolecular support selected from a membrane, a fibrous media, a polymeric coating or material, a metal organic framework, a monolith support, a bead, a filter, or a resin.

(11) In embodiment (11) is presented the material of embodiment (10), wherein the material is of formula (III):

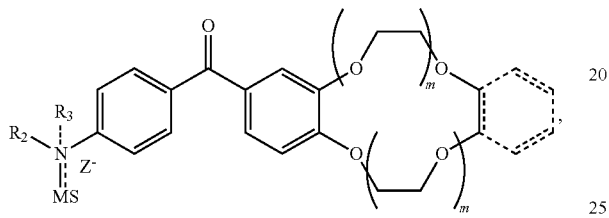

or a salt thereof, wherein each m independently is an integer from 1 to 8, $R_2$ is optionally present and is hydrogen or $C_{1-6}$ alkyl, each "⁓" designates an optionally present bond and/or structure, $R_3$ is optionally present and is hydrogen, $C_{1-6}$ alkyl, or MS, Z is optionally present and is a counterion to balance the charge on nitrogen, and each MS independently is a macromolecular support selected from a membrane, a fibrous media, a polymeric coating or material, a metal organic framework, a monolith support, a bead, a filter, or a resin.

(12) In embodiment (12) is presented the material of embodiment (10), wherein the material is of formula (IV):

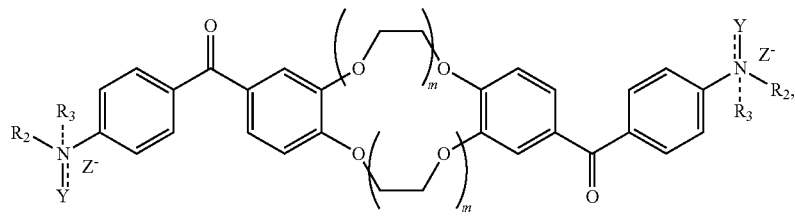

or a salt thereof, wherein each m independently is an integer from 1 to 8, each $R_2$ is optionally present and independently is hydrogen or $C_{1-6}$ alkyl, each "⁓" designates an optionally present bond and/or structure, each $R_3$ is optionally present and independently is hydrogen, $C_{1-6}$ alkyl, or MS, each Z is optionally present and independently is a counterion to balance the charge on nitrogen, each Y is $R_2$ or MS, provided that at least one Y is MS, and each MS independently is a macromolecular support selected from a membrane, a fibrous media, a polymeric coating or material, a metal organic framework, a monolith support, a bead, a filter, or a resin.

(13) In embodiment (13) is presented the material of any one of embodiments (10)-(12), wherein each m independently is an integer from 1 to 4.

(14) In embodiment (14) is presented the material of any one of embodiments (10)-(13), wherein each m independently is an integer selected from 1 or 2.

(15) In embodiment (15) is presented the material of any one of embodiments (10)-(14), wherein each m is 2.

(16) In embodiment (16) is presented the material of any one of embodiments (10)-(15), wherein each $R_2$ independently is hydrogen or $C_{1-6}$ alkyl.

(17) In embodiment (17) is presented the material of embodiment (16), wherein each $R_2$ is hydrogen.

(18) In embodiment (18) is presented the material of embodiment (16), wherein each $R_2$ is $C_{1-6}$ alkyl.

(19) In embodiment (19) is presented the material of any one of embodiments (10)-(18), wherein the macromolecular support comprises gelatin, alginate, starch, polyethylene, polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide, polyimide, polyester, cellulose, polystyrene, or a combination thereof.

(20) In embodiment (20) is presented a method of making a material of any one of embodiments (10)-(19), the method comprising:

(i) reacting a benzo or dibenzo crown ether with an aminobenzoic acid compound to form (a) a crown ether of formula (V):

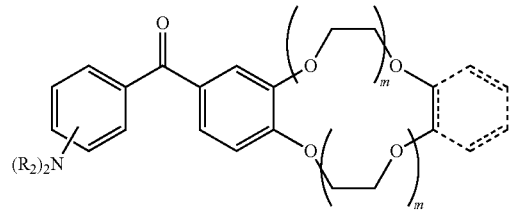

or (b) a crown ether of formula (VI):

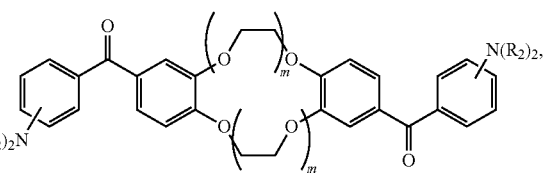

and (ii) reacting the crown ether of formula (V) or the crown ether of formula (VI) with a macromolecular support selected from a membrane, a fibrous media, a polymeric coating or material, a metal organic framework, a monolith support, a bead, a filter, or a resin to form at least one C—N bond or C=N bond.

(21) In embodiment (21) is presented the method of embodiment (20), wherein the aminobenzoic acid is 4-aminobenzoic acid, 4-(methylamino)benzoic acid, 4-(dimethylamino)benzoic acid, or a combination thereof.

(22) In embodiment (22) is presented a method of removing one or more metal ions from a solution comprising passing the solution through the material of any one of embodiments (1)-(19), or a salt thereof.

(23) In embodiment (23) is presented the method of embodiment (22), wherein the solution is an aqueous solution.

(24) In embodiment (24) is presented the method of embodiment (22) or embodiment (23), wherein the method removes at least 50% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

(25) In embodiment (25) is presented the method of embodiment (22) or embodiment (23), wherein the method removes at least 60% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

(26) In embodiment (26) is presented the method of embodiment (22) or embodiment (23), wherein the method removes at least 70% of one or more metal ions selected from sodium, magnesium, aluminum, potassium, calcium, titanium, vanadium, chromium, manganese, iron, cobalt, nickel, copper, zinc, molybdenum, cadmium, tin, barium, tungsten, lead, or a combination thereof.

EXAMPLES

These following examples further illustrate the invention but, of course, should not be construed as in any way limiting its scope.

Example 1

This example provides an exemplary experimental procedure for the preparation of a crown ether of formula (V), described herein, which is summarized in Scheme 1.

Scheme 1

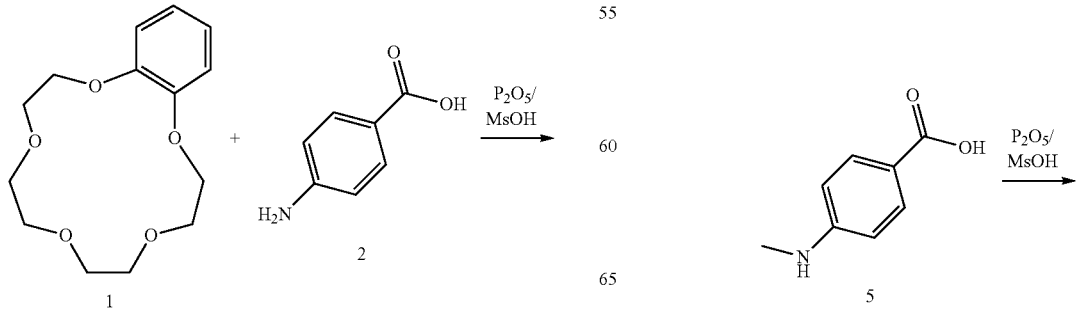

-continued

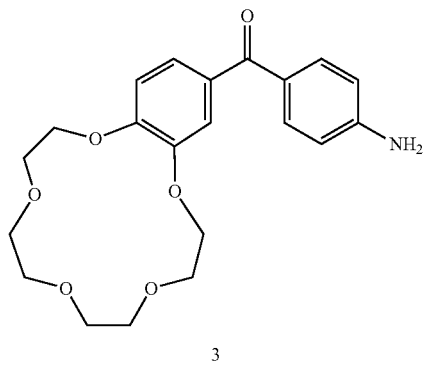

Benzo crown ether 1 (5 g, 18.6 mmol, 1 eq) was dissolved in Eaton's Reagent (35 g) at 50° C. Once fully dissolved, 4-aminobenzoic acid 2 (2.8 g, 20.5 mmol, 1.1 eq) was added and the reaction was heated at 50° C. for 16 hours. The resulting mixture was poured onto ice, filtered, and washed with water. After allowing the resulting solid product to dry on the filter, the product was recrystallized from ethanol to yield 2.23 g (31%) of aminobenzo crown ether 3.

Example 2

This example provides an exemplary experimental procedure for the preparation of a crown ether of formula (V), described herein, which is summarized in Scheme 2.

Scheme 2

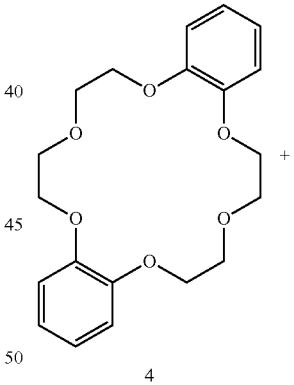

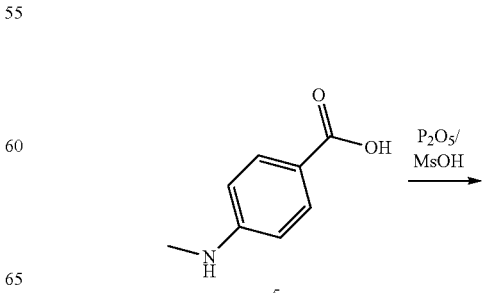

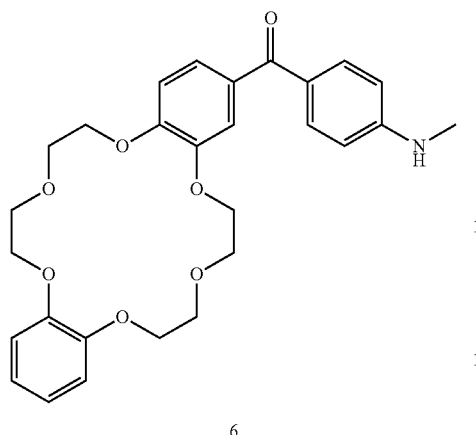

6

Dibenzo crown ether 4 (24.0 g, 66.5 mmol) was dissolved in Eaton's Reagent (110 mL) at 50° C. Once fully dissolved, 4-(methylamino)benzoic acid 5 (10.0 g, 66.5 mmol, 1 eq) was added and the reaction was heated at 50° C. for 4 hours. The resulting mixture was poured onto ice, filtered, and washed with water. After allowing the resulting solid product to dry on the filter, crude aminodibenzo crown ether 6 (30 g) was recovered. Nuclear magnetic resonance (NMR) spectroscopy indicated that the crude product was >85% of the desired product 6, with the mass balance being a mixture of starting material 4 and the double addition product.

Example 3

This example provides an exemplary experimental procedure for the preparation of a crown ether of formula (VI), described herein, which is summarized in Scheme 3.

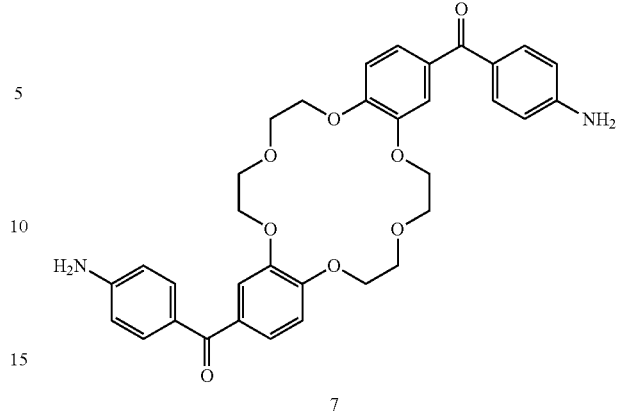

7

Dibenzo crown ether 4 (5.0 g, 13.8 mmol, 1 eq) was dissolved in Eaton's Reagent (35 g) at 50° C. Once fully dissolved, 4-aminobenzoic acid 2 (4.16 g, 30.4 mmol, 2.2 eq) was added and the reaction was heated at 50° C. for 4 hours. The resulting mixture was poured onto ice, filtered, and washed with water. After allowing the resulting solid product to dry on the filter, the product was recrystallized from ethanol to yield 4.1 g (50%) of diaminodibenzo crown ether 7.

Example 4

This example provides an exemplary experimental procedure for the preparation of a material of formula (III), described herein, which is summarized in Scheme 4.

Scheme 4

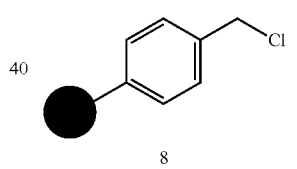

8

+

Scheme 3

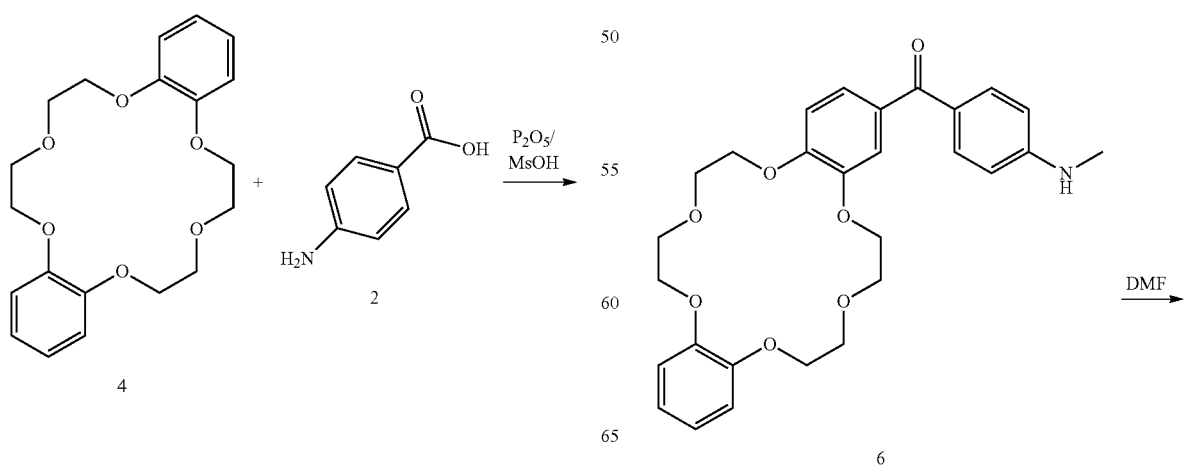

-continued

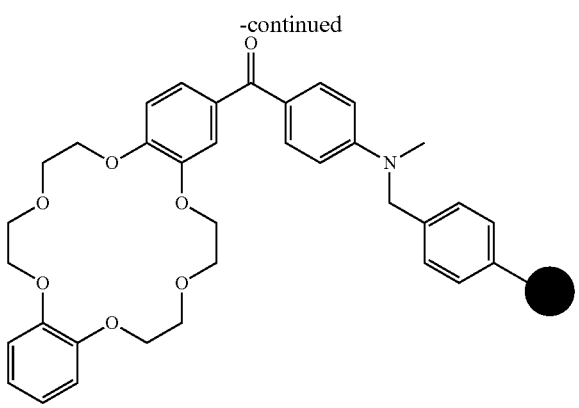

9

Aminodibenzo crown ether 6 (30 g, 60 mmol, 1.67 eq) was added to a solution of chloromethylated polystyrene: 1% divinylbenzene copolymer beads 8 (15 g, 36 mmol, 2.4 mmol/g) in DMF and the resulting solution was heated to 100° C. for 60 hours. The resulting mixture was poured onto ice, filtered, and washed with water. After allowing the resulting solid product to dry on the filter, aminodibenzo crown ether-modified polystyrene/divinylbenzene resin 9 (22.94 g, —0.7 molar eq/g) was obtained.

Example 5

This example demonstrates the metal removal efficiency of a material of formula (III), described herein.

Metal removal efficiency (MRE) testing was performed using 100 mg of the crown ether amine resin of Example 4, which has been cleaned with a 5% HCl solution and deionized water. A solution of water (50 mL), kept at a temperature of 94° C. in an oven, containing 6% LiOH and sodium, potassium, calcium, magnesium, or nickel in the initial concentrations set forth in Table 1 was passed through the resin using nitrogen gas at a rate of 7 mL/min. The challenge solution was collected in a vial and the resulting metal ion concentrations were measured by inductively coupled plasma-optical emission spectrometry (ICP-OES). The metal ion concentrations for three separate trials (n=1-3) are set forth in Table 1, and the metal removal efficiency (i.e., the percent concentration removed) was calculated. The metal removal efficiency results are set forth in Table 1 and plotted in the FIGURE.

As is apparent from the results set forth in Table 1 and the FIGURE, the crown ether amine resin of Example 4 removed greater than 50% of magnesium and nickel at 94° C., while selectively allowing ions such as lithium, sodium, potassium, and calcium to pass through. In other words, the crown ether amine resin of Example 4 was more effective at removing divalent cations than monovalent cations at 94° C.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

TABLE 1

Crown Ether Amine Resin Metal Removal Efficiency Results

| Metal Ion | Initial Concentration (ppm) | n = 1 Concentration (ppm) MRE (%) | n = 2 Concentration (ppm) MRE (%) | n = 3 Concentration (ppm) MRE (%) |
|---|---|---|---|---|
| $Na^+$ | 12.8 ppm | 13 ppm<br>0% | 13 ppm<br>0% | 13.3 ppm<br>0% |
| $K^+$ | 7.02 ppm | 7.15 ppm<br>0% | 7.2 ppm<br>0% | 7.42 ppm<br>0% |
| $Ca^{2+}$ | 10.8 ppm | 10.7 ppm<br>1% | 10.8 ppm<br>0% | 11.1 ppm<br>0% |
| $Mg^{2+}$ | 2.05 ppm | 0.7 ppm<br>66% | 0.19 ppm<br>91% | 0.43 ppm<br>79% |
| $Ni^{2+}$ | 2.3 ppm | 0.89 ppm<br>61% | 0.32 ppm<br>86% | 0.53 ppm<br>77% |

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A material comprising (i) a crown ether of formula:

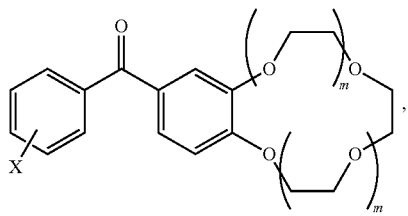

or a salt thereof, wherein each m independently is an integer from 1 to 8, X is $-N^*(R_1)$, $-N^{**}$, $-N^*(R_1)_2{}^+Z^-$, or $-N^{**}(R_1)^+Z^-$, wherein each $R_1$ independently is hydrogen or $C_{1-6}$ alkyl, Z is optionally present and independently is a counterion to balance the charge on nitrogen, and * represents a bond to a remainder of the material.

2. The material of claim 1, wherein each m independently is an integer from 1 to 4.

3. The material of claim 1, wherein each m independently is an integer selected from 1 or 2.

4. The material of claim 1, wherein X is $-N^*(R_1)$, or $-N^{**}$, wherein each $R_1$ independently is hydrogen or $C_{1-6}$ alkyl, and * represents a bond to a remainder of the material.

5. The material of claim 1, wherein the material is of formula (III):

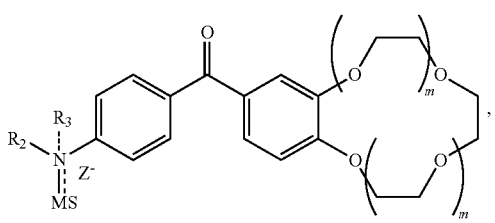

or a salt thereof, wherein each m independently is an integer from 1 to 8, $R_2$ is optionally present and is hydrogen or $C_{1-6}$ alkyl, each ⌇ designates an optionally present bond and/or structure, $R_3$ is optionally present and is hydrogen, $C_{1-6}$ alkyl, or MS, Z is optionally present and is a counterion to balance the charge on nitrogen, and each MS is a macromolecular support selected from a membrane, a fibrous media, a polymeric coating or material, a metal organic framework, a monolith support, a bead, a filter, or a resin.

6. The material of claim 5, wherein each m is an integer from 1 to 4.

7. The material of claim 5, wherein each m is an integer selected from 1 or 2.

8. The material of claim 5, wherein $R_2$ is hydrogen or $C_{1-6}$ alkyl.

9. The material of claim 5, wherein each macromolecular support comprises gelatin, alginate, starch, polyethylene, polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide, polyimide, polyester, cellulose, polystyrene, or a combination thereof.

10. A material comprising (i) a crown ether of formula:

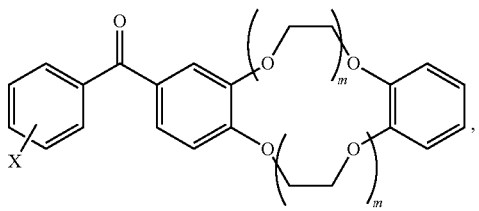

or a salt thereof, wherein each m is an integer from 1 to 8, X is $-N^*(R_1)$, $-N^{**}$, $-N^*(R_1)_2{}^+Z^-$, or $-N^{**}(R_1)^+Z^-$, wherein $R_1$ is hydrogen or $C_{1-6}$ alkyl, Z is optionally present and is a counterion to balance the charge on nitrogen, and * represents a bond to a remainder of the material.

11. The material of claim 10, wherein each m is an integer from 1 to 4.

12. The material of claim 10, wherein each m is an integer selected from 1 or 2.

13. The material of claim 10, wherein X is $-N^*(R_1)$, or $-N^{**}$, wherein $R_1$ independently is hydrogen or $C_{1-6}$ alkyl, and * represents a bond to a remainder of the material.

14. The material of claim 10, wherein the material is of formula (III):

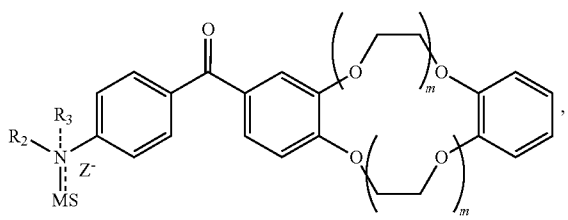

or a salt thereof, wherein each m is an integer from 1 to 8, $R_2$ is optionally present and is hydrogen or $C_{1-6}$ alkyl, each ⌇ designates an optionally present bond and/or structure, $R_3$ is optionally present and is hydrogen, $C_{1-6}$ alkyl, or MS, Z is optionally present and is a counterion to balance the charge on nitrogen, and each MS is a macromolecular support selected from a membrane, a fibrous media, a polymeric coating or material, a metal organic framework, a monolith support, a bead, a filter, or a resin.

15. The material of claim 14, wherein each m is an integer from 1 to 4.

16. The material of claim 14, wherein each m is an integer selected from 1 or 2.

17. The material of claim 14, wherein $R_2$ is hydrogen or $C_{1-6}$ alkyl.

18. The material of claim 14, wherein each macromolecular support comprises gelatin, alginate, starch, polyethylene, polypropylene, nylon, polyvinylidene fluoride, polyethylene oxide, polypropylene oxide, polyethylene/polypropylene oxide, polyacrylonitrile, poly(meth)acrylate, poly(meth)acrylamide, polyamide, polyimide, polyester, cellulose, polystyrene, or a combination thereof.

* * * * *